United States Patent [19]

Macdonald

[11] 4,303,754
[45] Dec. 1, 1981

[54] METHOD FOR OBTAINING 7β HYDROXY STEROIDS

[76] Inventor: Ian Macdonald, 604 Tower Rd., Halifax, Canada, B3H 4H7

[21] Appl. No.: 131,120

[22] Filed: Mar. 17, 1980

[51] Int. Cl.³ ............................................. C12P 33/00
[52] U.S. Cl. ........................................ 435/52; 435/58
[58] Field of Search ................................. 435/58, 52

[56] References Cited

U.S. PATENT DOCUMENTS 3,429,778  2/1969  Pan et al. ............................... 435/58

OTHER PUBLICATIONS

Charney et al., Microbial Transformations of Steroids, p. 347 (1967) Academic Press.

Primary Examiner—Alvin E. Tanenholtz

[57] ABSTRACT

Method of producing steroids having a 7β-OH substituent which comprises subjecting a steroid having a B-ring structure of the formula,

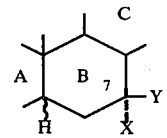

wherein X is OH; Y is H, and when taken together X and Y is oxo (O=), to the action of a microorganism of the genus *Clostridium*.

6 Claims, No Drawings

METHOD FOR OBTAINING 7β HYDROXY STEROIDS

This invention relates to the production of steroids and more particularly to steroids having an oxygenated substituent in the 7-position on the steroid nucleous. Even more particularly, this invention relates to the production of steroids possessing a B-ring structure of the following formula:

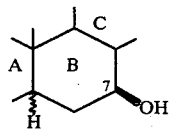

by a process which involves subjecting a steroid possessing a B-ring structure of the following formula:

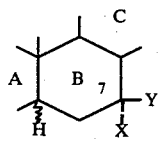

wherein X is OH, Y is H and when taken together X and Y is oxo (O=); to the actions of a microorganism of the genus Clostridium.

The final products producted by the practice of the process of the instant invention are steroid compounds which possess 7β-OH substituents. More particularly, the final products of this invention may be characterized generically as steroids which possess the following B-ring structure:

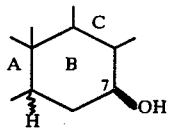

Even more particularly, the final products which may be produced by the practice of the instant invention are 7β-OH substituted steroids of the cholane group, and which include such specific steroid compounds as 3α, 7β-dihydroxy-5β-cholanoic acid; 3α, 7β, 12α-trihydroxy-5β-cholanoic acid and other like steroid compounds.

The starting materials which may be employed in the practice of this invention are also steroid compounds, and more particularly those steroid compounds which may be generically characterized as having the following B-ring structure:

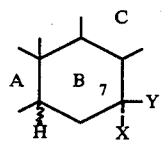

wherein X may be OH; Y may be H; and when taken together X and Y is oxo (O=). Preferably, in the practice of the instant invention, it has been found that satisfactory results may be obtained when the steroid starting materials possess the above identified B-ring structure and are also cholane derivatives. Most preferable results are obtained when the starting materials are cholanoic acid derivatives including such compounds as 3α, 7α, 12α-trihydroxy-cholanoic acid, 3α, 7α-dihydroxy cholanoic acid; 3α-hydroxy-7-oxo-cholanoic acid; 3α, 12α-dihydroxy-7-oxo-cholanoic acid, and other such compounds.

In this specification and the claims appended thereto, whenever a curved line ($\xi$) is employed in the chemical structures set forth herein in the linkage of atoms, it is meant to denote that the linked atom or substituent may be either in the alpha or beta-stereochemical position on the molecule as the case may be.

In order to produce the final products of this invention, the 7-oxygenated steroid starting materials are subjected to the action of the microorganisms which are employed in the practice of this invention. More particularly, the steroid starting materials may be subjected to the action of the enzymes of the desired microorganisms, or directly to the action of the microorganisms themselves under the proper conditions and in the necessary medium in which the microorganisms can be propagated in the presence of the desired starting steroid compounds. Depending on the nature of the enzyme producing microorganism to be utilized in the practice of this invention, the microorganism and the medium in which it may be grown can be varied to accommodate the specific microorganism involved, and may be modified depending on the results desired or the microorganism employed.

Among the microorganisms which may be employed in the practice of this invention may be generally included those enzyme producing microorganisms of the genus Clostridium. More particularly, the microorganisms which may be employed in the practice of this invention include such microorganisms as *Clostridium absonum*. Even more particularly, most satisfactory results have been obtained in the practice of this invention where the specific microorganism employed has been *Clostridium absonum* ATCC 27555, ATCC 27635, ATCC 27636, ATCC 27637, VPI 6903A, or *Clostridium absonum* Nakamura's strain, KZ1214, KZ1215, KZ1216, or KZ1218. These microorganisms have been deposited in various culture collections, for example, those designated with ATCC accession numbers have been deposited with the American Type Culture Collection; those designated with VPI accession numbers have been deposited with Virginia Polytechnic Institute and State University, Anaerobe Laboratory c/o Dr. L. V. Holdeman, Blacksburg, Va. 24060, U.S.A.; and those designated with KZ accession numbers have been deposited with Kanazawa University, School of Medicine, Dep't. of Bacteriology, c/o Dr. S. Nakamura, Kanazawa, Japan; and specimens thereof may be obtained in the usual manner as is known to the worker skilled in the art.

In general, the conditions of culturing the microorganisms which may be utilized in the practice of this invention are, except for the inclusion of the 7-substituted steroid starting material, the same as those employed in the propagation of like organisms for such purpose, i.e., the microorganism is grown either aerobically or anaerobically (depending on the microorganism employed, for example, Clostridium are generally propagated under anaerobic conditions) in contast with (in or on) a suitable fermentation medium. A suitable medium essentially comprises a source of carbon and energy. The latter may be a carbohydrate, a fatty acid, a fat and/or the 7 substituted steroid starting material itself. Among the fats employable are lard oil, soybean oil, linseed oil and the like, all of which are well known to the skilled worker. Among the fatty acids may be included stearic acid, palmetic acid and other like materials. The source of the required nitrogenous factors may be organic, for example, soybean meal, corn steep liquor and/or distiller's solubles, or it may be synthetic, i.e., composed of synthesizable organic or inorganic compounds such as, ammonium salts, alkali nitrates, amino acids, or urea.

For aerobic fermentation, an adequate, sterile air supply should be maintained. For anaerobic fermentation, external sources of oxygen should be excluded from the fermentation vessels. The 7-substituted steroid starting material may be added to the culture during the incubation period, or included in the medium prior to sterilization or inoculation. A satisfactory (but not limiting) range of concentration of the 7-substituted starting material, for example, $3\alpha$, $7\alpha$-dihydroxy-$5\beta$-cholanoic acid (Chenodeoxycholic Acid) in the culutre can range from about 0.001 to about 1.0%, however, this concentration may be varied and adjusted depending upon the ability of the microorganism to properly grow in the resulting media. The culturing period, or rather the time of subjecting the 7-substituted steroid starting materials to the action of the enzymes produced by these microorganisms while they are propagating, may vary considerably, the range of from 4 to 96 hours being feasible, but not limitative. In addition, the pH range of the culture medium may also be varied from about 5.0 to 9.0 without any substantial untoward effects on the desired results obtained.

In addition to the foregoing, it is also possible in the practice of this invention to obtain equivalent results by employing cell free solutions of the enzyme materials produced by the propagation of the desired Clostridia organisms. These cell free compositions may be obtained in any manner known to the skilled worker, for example, ultrasonic cell disruption techniques when employed in conjunction with proper filtering and collection methods will provide satisfactory results. However, when cell free preparations are employed in the practice of this invention, it has been found necessary to employ an NADP-coenzyme, which may be prepared and employed in accordance with procedures which are well known and accepted by the skilled worker in the art.

The following Examples are illustrative of the invention:

EXAMPLE 1

The organism *Clostridium absonum* (VPI 6903A) is maintained in a chopped meat culture at 4° C. A volume of 1 ml. taken from this chopped meat starter culture is introduced into a 40 ml. volume of freshly autoclaved brain-heart infusion (Barto Brain Heart Infusion B37, Difco Laboratories) broth containing 0.1% thioglycollate. The culture is grown for 12 hours at 37° C., after which it is transferred into 1.0 liter of brain-heart infusion broth containing 0.1% thioglycollate and $5 \times 10^{-4}$ M $3\alpha$, $7\alpha$-dihydroxy-$5\beta$-cholanoic acid (Chenodeoxycholic Acid). The resultant culture is allowed to grow for 12 hours at 37° C., at which time it is then acidified to pH 3 with HCl and extracted three times with ether. The combined ether extracts were then washed with water, dried over sodium sulfate and evaporated to dryness in vacuo to yield 160 mg of $3\alpha$, $7\beta$-dihydroxy-$5\beta$-cholanoic acid (yield by thin layer chromatography = 70–80%).

EXAMPLE 2

The procedure of Example 1 is followed except that equivalent amounts of the following organisms were substituted for the *Clostridium absonum* VPI 6903A to yield equivalent results: *Clostridium absonum* ATCC 27555; *Clostridium absonum* ATCC 27637 and *Clostridium absonum* Nakamura's strain KZ1216.

EXAMPLE 3

The procedure of Example 1 is followed except than an equivalent amount of $3\alpha$-hydroxy-7-keto-$5\beta$-cholanoic acid is substituted for the $3\alpha$, $7\alpha$-dihydroxy-$5\beta$-cholanoic acid, thus yielding $3\alpha$, $7\beta$-dihydroxy-$5\beta$-cholanoic acid (ursodeoxycholic acid).

EXAMPLE 4

The procedure of Example 1 is followed except that an equivalent amount of $3\alpha$, $7\alpha$, $12\alpha$-trihydroxy-$5\beta$-cholanoic acid (cholic acid) is substituted for the $3\alpha$, $7\alpha$-dihydroxy-$5\beta$-cholanoic acid, to yield $3\alpha$, $7\beta$, $12\alpha$-trihydroxy-$5\beta$-cholanoic acid.

EXAMPLE 5

The procedure of Example 1 is followed except that an equivalent amount of $3\alpha$, $12\alpha$-dihydroxy-7-keto-$5\beta$-cholanoic acid is substituted for the $3\alpha$, $7\alpha$-dihydroxy-$5\beta$-cholanoic acid to yield $3\alpha$, $7\beta$, $12\alpha$-trihydroxy-$5\beta$-cholanoic acid.

The invention may be variously otherwise embodied within the scope of the appended claims.

What is claimed is:

1. A method for producing $7\beta$-OH substituted steroids which comprises subjecting a cholane steroid compound having a B-ring structure of the following formula:

wherein X is OH, Y is H and when taken together X and Y is oxo (O=); to the action of a *Clostridium absonum* microorganism.

2. The method of claim 1 wherein the steroid compound is selected from the group consisting of chenodeoxycholic acid, 7-ketolithocholic acid, cholic acid, and 7-ketodeoxycholic acid to the action of a *Clostridium absonum* microorganism.

3. A method for producing ursodeoxycholic acid which comprises subjecting chenodeoxycholic acid to the action of the enzymes produced by the microorganism *Clostridium absonum* in a suitable medium.

4. The method of claim 3, wherein chenodeoxycholic acid is subjected to the action of enzymes produced by the microorganism *Clostridium absonum* in a suitable medium and there is recovered ursodeoxycholic acid.

5. The method of claim 1 wherein the steroid compound is chenodeoxycholic acid.

6. The method of obtaining $7\beta$-OH substituted steroids which comprises subjecting a cholane steroid compound having a B-ring structure as set forth in claim 1, to the action of a *Clostridium absonum* microorganism and recovering the $7\beta$-OH steroid produced.

* * * * *